(12) United States Patent
Purwar et al.

(10) Patent No.: US 11,894,161 B2
(45) Date of Patent: Feb. 6, 2024

(54) SYSTEMS AND METHODS FOR ENERGY MODULATED RADIATION THERAPY

(71) Applicant: Varian Medical Systems, Inc., Palo Alto, CA (US)

(72) Inventors: Anuj K. Purwar, Fremont, CA (US); James E. Clayton, Saratoga, CA (US); Dragos E. Constantin, Los Altos, CA (US); Gard E. Meddaugh, Mountain View, CA (US); Matthew C. Schmidt, Henderson, NV (US); Mark E. Trail, Menlo Park, CA (US); Flavio Poehlmann, Fremont, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 783 days.

(21) Appl. No.: 16/833,424

(22) Filed: Mar. 27, 2020

(65) Prior Publication Data

US 2020/0227184 A1 Jul. 16, 2020

Related U.S. Application Data

(63) Continuation of application No. 15/470,803, filed on Mar. 27, 2017, now Pat. No. 10,622,114.

(51) Int. Cl.
*G21K 1/093* (2006.01)
*A61N 5/10* (2006.01)
*G21K 5/04* (2006.01)

(52) U.S. Cl.
CPC ........... *G21K 1/093* (2013.01); *A61N 5/1043* (2013.01); *G21K 5/04* (2013.01); *A61N 2005/1087* (2013.01)

(58) Field of Classification Search
CPC .................. G21K 1/093; A61N 5/1071; A61N 2005/1087; A61N 5/1067; A61N 5/1082
See application file for complete search history.

(56) References Cited

U.S. PATENT DOCUMENTS 3,546,524 A 12/1970 Stark
3,714,592 A 1/1973 Jory
(Continued)

FOREIGN PATENT DOCUMENTS

EP 994638 A1 * 4/2000 ............... H05H 7/10
JP 2016031849 A 3/2016

OTHER PUBLICATIONS

S.F. De Boer, et al., "The effect of beam energy on the quality of IMRT plans for prostate conformal radiotherapy," Technol. Cancer Res. Treat. 6, 139-146, 2007, 8 pages.
(Continued)

*Primary Examiner* — Christine H Matthews
*Assistant Examiner* — Joshua Daryl D Lannu
(74) *Attorney, Agent, or Firm* — Harness, Dickey & Pierce, P.L.C.

(57) ABSTRACT

A method performed by a medical device, includes: providing a permanent magnetic field by a permanent magnet; operating an electromagnet to provide a first electromagnetic field with a first electromagnetic field value; and operating the electromagnet to provide a second electromagnetic field with a second electromagnetic field value; wherein the first electromagnetic field and the permanent magnetic field forms a first total magnetic field with a first total magnetic field value, and wherein the second electromagnetic field and the permanent magnetic field forms a second total magnetic field with a second total magnetic field value; wherein the first total magnetic is formed when an electric field in an accelerator or an energy level of a particle beam has a first value, and wherein the second total magnetic field is formed when the electric field in the accelerator or the energy level of the particle beam has a second value.

23 Claims, 9 Drawing Sheets

(56) References Cited

U.S. PATENT DOCUMENTS

| | | | |
|---|---|---|---|
| 3,820,035 A | 6/1974 | Meddaugh | |
| 4,286,192 A | 8/1981 | Tanabe et al. | |
| 4,382,208 A | 5/1983 | Meddaugh et al. | |
| 4,425,506 A | 1/1984 | Brown et al. | |
| 5,487,401 A * | 1/1996 | Johnson | A45B 25/20 135/33.7 |
| 6,366,021 B1 | 4/2002 | Meddaugh et al. | |
| 7,295,649 B2 | 11/2007 | Johnsen | |
| 7,339,320 B1 | 3/2008 | Meddaugh et al. | |
| 8,198,587 B2 | 6/2012 | Whittum et al. | |
| 8,378,312 B1 * | 2/2013 | Gordon | G21K 1/093 250/396 R |
| 2004/0213375 A1 * | 10/2004 | Bjorkholm | H01J 35/24 378/58 |
| 2007/0215813 A1 | 9/2007 | Whittum et al. | |
| 2013/0023716 A1 * | 1/2013 | Thomas | A61N 5/1071 600/1 |
| 2013/0026388 A1 * | 1/2013 | Claereboudt | A61N 5/1043 250/397 |
| 2014/0014849 A1 * | 1/2014 | Anferov | H01J 3/26 250/396 R |
| 2014/0031602 A1 * | 1/2014 | Fujimoto | A61N 5/1043 378/204 |
| 2014/0094639 A1 * | 4/2014 | Zwart | H05H 13/02 315/502 |
| 2014/0099918 A1 * | 4/2014 | Lisi | H04M 15/00 455/406 |
| 2014/0252994 A1 * | 9/2014 | Trbojevic | H05H 13/085 315/503 |
| 2014/0371511 A1 * | 12/2014 | Zwart | A61N 5/1077 315/502 |
| 2016/0141062 A1 | 5/2016 | Zhang et al. | |

OTHER PUBLICATIONS

Jong Min Park, et al., "Photon energy-modulated radiotherapy: Monte Carlo simulation and treatment planning study", Med. Phys. 39, 1265, 2021, 13 pages.

* cited by examiner

SYSTEMS AND METHODS FOR ENERGY MODULATED RADIATION THERAPY

RELATED APPLICATION DATA

This application is a continuation of U.S. patent Ser. No. 15/470,803, filed on Mar. 27, 2017, pending. The entire disclosure of the above application is expressly incorporated by reference herein.

FIELD

The field of the application relates to treatment systems, and more particularly, to systems and methods for energy modulated radiation therapy.

BACKGROUND

Radiation therapy involves medical procedures that selectively deliver high doses of radiation to certain areas inside a human body. A radiation machine for providing radiation therapy includes an electron source that provides electrons, and an accelerator that accelerates the electrons to form an electron beam. The electron beam is delivered downstream where it strikes a target to generate radiation. The radiation is then collimated to provide a radiation beam having a certain desired characteristic for treatment purpose. In other cases, instead of radiation, a particle beam (e.g., electron beam, proton beam, etc.) may be used as treatment energy to treat the patient.

Systems and methods for energy modulated radiation therapy is described herein.

SUMMARY

A method performed by a medical device, includes: providing a permanent magnetic field by a permanent magnet; operating an electromagnet to provide a first electromagnetic field with a first electromagnetic field value; and operating the electromagnet to provide a second electromagnetic field with a second electromagnetic field value; wherein the first electromagnetic field and the permanent magnetic field forms a first total magnetic field with a first total magnetic field value, and wherein the second electromagnetic field and the permanent magnetic field forms a second total magnetic field with a second total magnetic field value; wherein the first total magnetic is formed when an electric field in an accelerator or an energy level of a particle beam has a first value, and wherein the second total magnetic field is formed when the electric field in the accelerator or the energy level of the particle beam has a second value.

Optionally, the permanent magnet comprises a rare earth magnet.

Optionally, the electromagnet comprises a coil surrounding the permanent magnet.

Optionally, the method further includes: providing the particle beam by the accelerator; and changing the energy level of the particle beam by an energy switch.

Optionally, the energy level of the particle beam is changed within a duration that is less than one second.

Optionally, the accelerator comprises a fixed-field alternating gradient (FFAG) accelerator, or a non-scaling fixed-field alternating gradient (NS-FFAG) accelerator.

Optionally, the method further includes adjusting a parameter in a dosimetry circuit in correspondence with the electric field in the accelerator or the energy level of the particle beam.

Optionally, the dosimetry circuit is a part of an ion chamber.

Optionally, the electromagnet comprises a laminated steel.

Optionally, one of the acts of operating the electromagnet comprises increasing the current of the electromagnet in correspondence with an increase in the electric field in the accelerator or the energy level of the particle beam.

Optionally, one of the acts of operating the electromagnet comprises decreasing the current of the electromagnet in correspondence with a decrease in the electric field in the accelerator or the energy level of the particle beam.

Optionally, the electromagnet comprises a pretzel magnet.

Optionally, the electromagnet is a part of a beam deflector, wherein a beam output is coupled to the beam deflector, and wherein the method further comprises moving the beam output to deliver treatment energy from a plurality of gantry angles that includes at least a first gantry angle and a second gantry angle.

Optionally, the method further includes adjusting the treatment energy so that the treatment energy has a first treatment energy level when the beam output is at the first gantry angle, and a second treatment energy level when the beam output is at the second gantry angle.

Optionally, the treatment energy is adjusted by an energy adjuster in a continuous manner.

Optionally, the treatment energy is adjusted by an energy adjuster in a discrete manner.

Optionally, the method further includes adjusting the treatment energy so that the treatment energy has a first treatment energy level when the beam output is at the first gantry angle, and a second treatment energy level when the beam output is at the first gantry angle.

Optionally, the treatment energy is outputted without using any flattening filter.

Optionally, the electromagnet is operated such that a trajectory of the particle beam remains the same regardless of the energy level of the electric field in the accelerator or the energy level of the particle beam.

A treatment method, includes: configuring a medical system for delivering a first treatment beam having a first energy level; delivering the first treatment beam by the medical system towards a patient that is on a patient support; configuring the medical system for delivering a second treatment beam having a second energy level; and delivering the second treatment beam by the medical system towards the patient; wherein the act of configuring the medical system for delivering the second treatment beam comprises changing an energy that is associated with an accelerator by an energy switch, and adjusting a current of an electromagnet by a current control in correspondence with the energy associated with the accelerator; wherein the first treatment beam is delivered towards the patient from a first gantry angle, and the second treatment beam is delivered towards the patient from a second gantry angle.

Optionally, the medical system comprises an ion chamber, wherein the ion chamber comprises a dosimetry circuit, and wherein the method further comprises adjusting a parameter in the dosimetry circuit in correspondence with the energy associated with the accelerator.

Optionally, the acts of configuring the medical system, and the acts of delivering are performed so that the first treatment beam transitions to the second treatment beam in a continuous manner.

Optionally, the acts of configuring the medical system, and the acts of delivering are performed so that the first treatment beam and the second treatment beam are delivered in a discrete manner.

Optionally, the energy associated with the accelerator comprises an electric field in the accelerator or an energy level of a particle beam in the accelerator.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
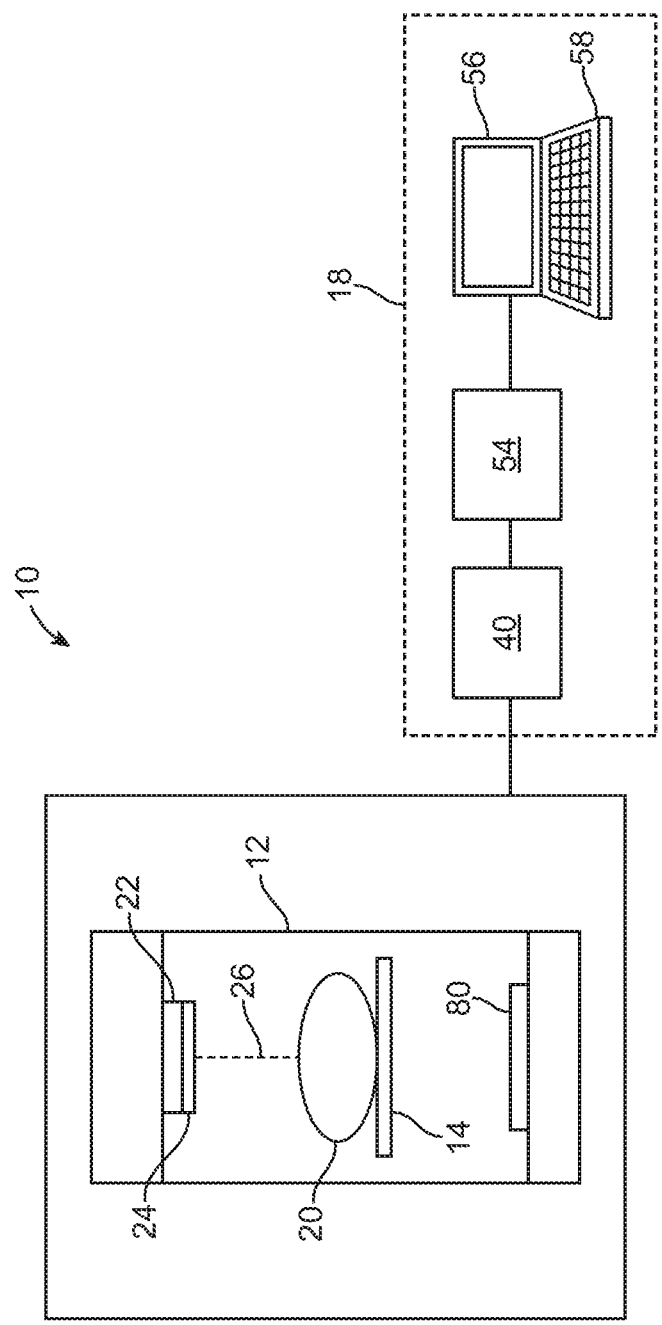
FIG. 1 illustrates a radiation treatment system.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate a proton beam, electron beam, or neutron beam, as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to generate X-ray radiation at a plurality of photon energy levels within a range anywhere between approximately 10 keV and approximately 20 MeV. Alternatively, the source 22 may not be a radiation source, and may instead be a particle source configured to provide a particle beam (e.g., electron beam, proton beam, etc.) as treatment beam. In other embodiments, the source 22 may be configured to provide a combination of photon beam and particle beam (e.g., electron beam, proton beam, etc.) for treatment. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

Figure 2A:
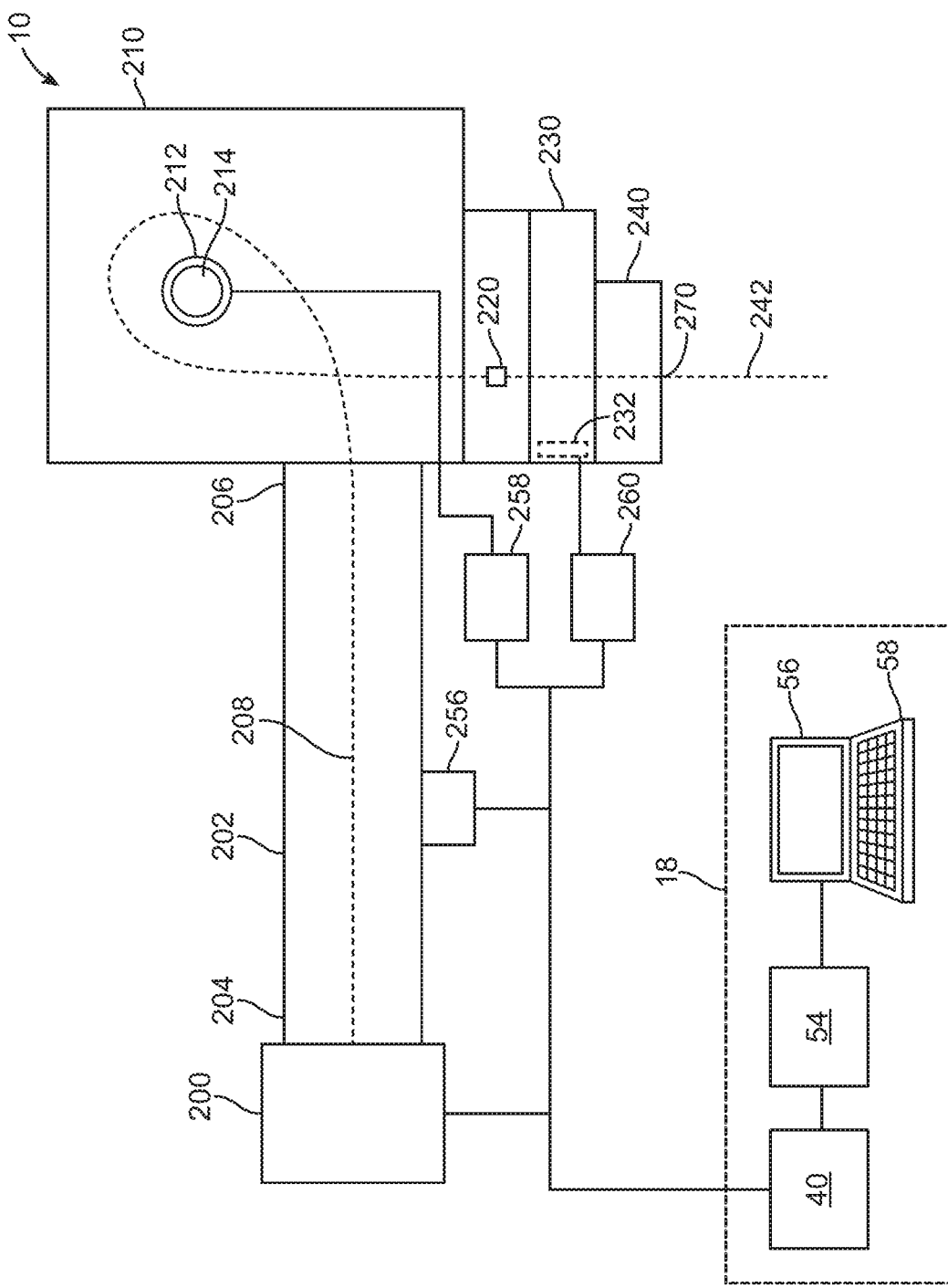
FIG. 2A illustrates an example of some components of the radiation system of FIG. 1.

FIG. 2A illustrates some of the components of the radiation treatment system 10. As shown in the figure, the radiation treatment system 10 includes an electron source 200 for generating and providing electrons. The radiation treatment system 10 also includes a particle accelerator 202 having a first end 204 and a second end 206. The first end 204 of the accelerator 202 is coupled to the electron source 200 for receiving the electrons. The accelerator 202 is configured to accelerate the electrons to form an electron beam 208. The radiation treatment system 10 further includes a beam deflector 210 configured to turn the direction of the electron beam 208. As shown in the figure, the beam deflector 210 includes an electromagnet 212 and a permanent magnet 214. In other embodiments, the beam deflector 210 may include only the electromagnet 212 without the permanent magnet 214. In the illustrated example, the radiation treatment system 10 also includes a target 220 for receiving the electron beam 208. The electrons in the electron beam 208 strike the target 220 to generate radiation. The radiation goes through an ion chamber 230 configured to measure a dose associated with the radiation. The radiation is then collimated by a collimator 240 into a desired radiation beam 242.

In the illustrated embodiments, the radiation treatment system 10 is configured to provide variable treatment energies for treating a patient. The radiation treatment system 10 also includes an energy switch 256 coupled to the accelerator 202 for changing an energy (e.g., an energy level) associated with the accelerator 202. The radiation treatment system 10 also includes a current control 258 for adjusting a current for the electromagnet 212, and a control 260 for adjusting a parameter in a dosimetry circuit 232 of the ion chamber 230 in correspondence with the energy associated with the accelerator 202.

In the illustrated figure, the current control 258 and the control 260 are shown as separate components from the control 40. In other embodiments, the current control 258 and/or the control 260 may be integrated with the control 40 of the radiation treatment system 10.

During use, the electron source 200 generates electrons and feeds the electrons to the accelerator 202. The accelerator 202 accelerates the electrons to form an electron beam 208 that travels down the longitudinal axis of the accelerator 202. The accelerator 202 is excited by a power, e.g., microwave power, delivered by a Magnetron (not shown) at a frequency, for example, between 1000 MHz and 20 GHz, and more typically, between 2800 and 3000 MHz. In other embodiments, the Magnetron can have other configurations and/or may be configured to provide power at other frequencies. The power delivered by the Magnetron may be in a form of electromagnetic waves. In other embodiments, instead of Magnetron, a klystron may be used. The electrons generated by the electron source 200 are accelerated through the accelerator 202 by oscillations of the electromagnetic fields within cavities of the accelerator 202, thereby resulting in the electron beam 208 having certain level of energy.

The electron beam 208 exits the second end 206 of the accelerator 202 and is deflected by the beam deflector 210 at the second end 206 of the accelerator 202. In the illustrated embodiments, the control 40 controls the energy switch 256 so that the electron beam 208 exiting the accelerator 202 will have a first energy level. The current control 258 is configured to adjust a current for the electromagnet 212 in the beam deflector 210 in correspondence with an energy (e.g., energy level) associated with the accelerator 202. In some embodiments, the energy associated with the accelerator 202 may be an energy level of an electric field in the accelerator 202 caused or to be caused by an operation of the energy switch 256. In other embodiments, the energy associated with the accelerator 202 may be the energy level of the electron beam 208 generated or to be generated by the accelerator 202. As the energy of the electron beam 208 is increased, more magnetic field energy is provided by the electromagnet 212 in order to change the direction of the electron beam 208 by a certain pre-determined angle. Similarly, as the energy of the electron beam 208 is decreased, less magnetic field energy is provided by the electromagnet 212 to change the direction of the electron beam 208 by the same pre-determined angle. In the illustrated example, the electron beam 208 is deflected by 270° using the beam deflector 210. In other embodiments, the beam deflector 210 may be configured to deflect the electron beam 208 by other range of angles.

In the illustrated example, the electromagnet 212 is surrounding the permanent magnet 214. The electromagnet 212 is configured to provide a first magnetic field MF1, and the permanent magnet 214 is configured to provide a second magnetic field MF2. The combined magnetic field MFT will thus be MF1+MF2. In some cases, the magnetic field MF2 provided by the permanent magnet 214 corresponds with the lowest energy level of the radiation beam that is to be generated. For example, if the system 10 is configured to provide a radiation beam having an energy level that ranges from 2 MeV to 20 MeV, then the permanent magnet 214 may be configured to provide the magnetic field MF2 that corresponds with the energy level of 2 MeV for the radiation beam. In such cases, the electromagnet 212 is configured to provide the magnetic field that ranges from 0 to MF1 (depending on the amount of current provided for the coils of the electromagnet 212), wherein the combined magnetic field of MF2+0 corresponds with the beam energy level of 2 MeV, and the combined magnetic field of MF2+MF1 corresponds with the beam energy level of 20 MeV. Accordingly, the combination of the electromagnet 212 and the permanent magnet 214 provides an unique combined magnetic field for each of the available beam energy levels.

In other embodiments, the magnetic field MF2 provided by the permanent magnet 214 corresponds with a beam energy level that is lower than the lowest energy level of the radiation beam to be generated. For example, if the system 10 is configured to provide a radiation beam having an energy level that ranges from 2 MeV to 20 MeV, then the permanent magnet 214 may be configured to provide the magnetic field MF2 that corresponds with a beam energy level of 1 MeV. In such cases, the electromagnet 212 is configured to provide the magnetic field that ranges from 0 to MF1 (depending on the amount of current provided for the coils of the electromagnet 212), wherein the combined magnetic field of MF2+0 corresponds with the beam energy level of 1 MeV, and the combined magnetic field of MF2+MF1 corresponds with the beam energy level of 20 MeV.

Also, in other embodiments, the electromagnet 212 may not surround the permanent magnet 214. Instead, the electromagnet 212 may be placed next to the permanent magnet 214 in a side-by-side configuration.

In some embodiments, the permanent magnet 214 may be implemented using a rare earth permanent magnet. By using a rare earth magnet that is precisely machined and positioned, the amount of electromagnet needed to generate a desired magnetic field may be reduced. Furthermore, in other embodiments, instead of one electromagnet 212 and/or one permanent magnet 214, the beam deflector 210 may include multiple electromagnets and/or multiple permanent magnets.

It should be noted that the combination of the electromagnet 212 and the permanent magnet 214 is advantageous because it allows a range of magnetic fields to be generated, while reducing the size of the beam deflector 210 (compared to the scenario in which just electromagnet is used). This in turn, provides a compact head (i.e., the structure upstream from the collimator 240) allowing more clearance to the patient and/or room walls. The hybrid bend magnet is also cheaper to construct and maintain due to smaller electromagnet with fewer copper windings (compared to the scenario in which just electromagnet is used), and due to lower amount of electrical current and cooling involved in the operation of the hybrid bend magnet. Furthermore, the hybrid bend magnet has the benefit of reducing magnetic hysteresis, which allows faster switching of energy of the electron beam. In some embodiments, the bend magnet's energy hysteresis cycle may be speed up by using laminated steel. Other materials may be used for the bend magnet in other embodiments.

After the electron beam 208 is deflected by the beam deflector 210, the electron beam 208 strikes the target 220 to generate radiation. Alternatively, the electron beam 208 may not strike any target, and instead be used directly as treatment energy. Also, in other embodiments, instead of electron beam, the accelerator may provide other particle beams, such as proton beam, for treatment. The radiation or beam goes through the ion chamber 230 that measures a dose associated with the radiation or the beam. The dosimetry circuit 232 of the ion chamber 230 is configured to calculate a dose based on the radiation or energy received and one or more parameters (e.g., a dose calculation parameter). In the illustrated embodiments, the control 260 is configured to adjust a parameter (e.g., a dose calculation parameter) at the dosimetry circuit 232 in correspondence with the energy associated with the accelerator 202. As similarly discussed, the energy associated with the accelerator 202 may be an energy level of an electric field in the accelerator 202 caused or to be caused by an operation of the energy switch 256, or an energy level of the electron beam 208 that is generated or to be generated.

The control 260 is advantageous because as the energy level of the electron beam 208 changes, the relation between the radiation energy and dose may not be constant. The control 260 allows the dosimetry circuit 232 of the ion chamber 230 to be updated so that ionization from changing energies is handled correctly. In particular, in order to correctly calculate a dose value associated with the generated radiation, the dose calculation parameter in the dosimetry circuit 232 is adjusted by the control 260. In one implementation, the relation between the different energy levels associated with the accelerator 202 and dose values may be determined empirically, and the resulting relation may then be programmed into the control 260 so that the control 260 can determine how much to adjust the dose calculation parameter based on the energy level associated with the accelerator 202. In other embodiments, the relation may be determined mathematically.

After the radiation goes through the ion chamber 230, the radiation is then collimated by the collimator 240 into a desired radiation beam 242. In some embodiments, the collimator 240 may be a multi-leaves collimator having a plurality of moveable fingers configured to shape a cross section of the radiation beam 242. In other embodiments, the collimator 240 may be a block collimator, or any other types of collimator.

In some embodiments, the control 40 is configured to operate the energy switch 256, the current control 258, and the control 260 in correspondence with each other so that a radiation beam 242 with a desired characteristic is provided at a beam output 270 as defined by the collimator 240. Also, in some embodiments, the operation of the energy switch 256, the current control 258, and the control 260 may be performed in synchronization with each other.

In other embodiments, instead of the control 40 controlling the energy switch 256, the current control 258, and the control 260, the operation of the energy switch 256 and/or the control 260 may be based on a configuration of the energy switch 256. In one implementation, the energy switch 256 may include a probe that is moveably mounted to a cavity. In such cases, by varying an amount of insertion of the probe into the cavity, the energy associated with the accelerator 202 may be adjusted. In some embodiments, the operation of the current control 258 and/or the control 260 may be based on an amount of insertion of the probe into the cavity at the energy switch 256. The energy switch 256 may include a sensor for measuring an amount of insertion by the probe into the cavity. Based on the sensed value (representing the amount of insertion of the probe, and also representing the energy associated with the accelerator 202), the current control 258 may then adjust the current for the electromagnet 212. Similarly, based on the sensed value (representing the amount of insertion of the probe, and also representing the energy associated with the accelerator 202), the control 260 may then adjust the parameter in the dosimetry circuit 232 at the ion chamber 230.

In further embodiments, the operation of the current control 258 and/or the control 260 may occur before the operation of the energy switch 256. For example, in one implementation, the current control 158 may be configured to first adjust the current for the electromagnet 212 so that the magnetic field for deflecting the electron beam 208 corresponds with an energy level of the electron beam 208 to be achieved. Then in response to the adjustment of the current, the energy switch 256 changes the energy level associated with the accelerator 202 so that the desired energy level of the electron beam 208 is achieved. The control 260 may also change the parameter in the dosimetry circuit 232 in correspondence with the adjusted current for the electromagnet 212.

In another example, the control 260 may be configured to first adjust the parameter in the dosimetry circuit 232 so that the operation of the dosimetry circuit 232 will correspond with an energy level of the electron beam 208 to be achieved. Then in response to the adjustment in the dosimetry circuit 232, the energy switch 256 changes the energy level associated with the accelerator 202 so that the desired energy level of the electron beam 208 is achieved. Also, in response to the adjustment in the dosimetry circuit 232, the current control 158 then adjusts the current for the electromagnet 212 so that the magnetic field for deflecting the electron beam 208 corresponds with the energy level of the electron beam 208 to be achieved.

In another example, the operation of the energy switch 256, the current control 258, and the control 260 may occur simultaneously or substantially simultaneously (e.g., within 1 second, or preferably within 0.5 second, and more preferably within 0.1 second).

The configuration of the system 10 is advantageous because it allows an energy of the electron beam 208 (and also the energy of the resulting radiation beam 242) to be changed during treatment. The change of the energy can occur quickly, such as within 3 seconds, and preferably within 1 second, and more preferably within 0.5 second, and even more preferably within 0.1 second. In some cases, the system 10 allows intra field switching of energy. The system 10 may also allow changes of energy while the gantry is rotating (e.g., as in RapidArc treatments).

In some embodiments, the system 10 may allow a first treatment beam with a first energy to be delivered to the patient from a first gantry angle, and a second treatment beam with a second energy to be delivered to the patient from a second gantry angle. In one implementation, the first treatment beam with the first energy is delivered to the patient while the gantry 12 is at the first gantry angle. The system 10 then stops the delivery of treatment beam, and moves the gantry 12 to the second gantry angle. The system 10 then delivers the second treatment beam with the second energy to the patient while the gantry 12 is at the second gantry angle.

In other embodiments, instead of discretely changing the energy in a step-wise manner, the system 10 may continuously change the energy level of the treatment beam while the treatment beam is being delivered towards the patient. For example as the gantry 12 rotates from the first gantry angle to the second gantry angle, the treatment beam may remain "on" and the energy of the treatment beam may be changed continuously from a first level to a second level. As another example, the continuous change of the energy level may be performed by the system 10 while the gantry 12 is at a certain gantry position. Furthermore, in some cases, while the gantry 12 is at a certain gantry position, the system 10 may perform intensity-modulate radiotherapy (IMRT). The IMRT may be performed using the collimator 24, or using both the collimator 24 and the switching of the energy. In some embodiments, the change of the energy may be discrete change in IMRT fields. In other embodiments, the change of the energy may be continuous change in the IMRT fields. The IMRT fields may utilize a step-and-shoot scheme, or a sliding window technique.

Also, in some embodiments, the change of the energy may be performed on a field-by-field basis.

In addition, allowing changes in energy in the radiation treatment is advantageous. This is because different radiation beam energies have different penetrating powers. For example, a beam energy of 6 MV may achieve a maximum dose at a depth of 1.6 cm below a skin of the patient, while a beam energy of 15 MV may achieve a maximum dose at a depth of 2.9 cm. Thus, higher energy beam may be utilized to reach deeper tumors. In some embodiments, fast and automated energy change may be performed during treatment to maximize dose conformity through difference in depth doses. Also, low energy radiation (e.g., below 6 MV) may have better dose falloff, leading to lower dose to normal tissue. Accordingly, the ability for the system 10 to change energy for different treatment fields will increase conformity to the tumor while reducing integral dose to normal tissue.

In one treatment technique, if a beam direction from a certain gantry angle traverses a tumor that is relatively close to the patient's skin, then lower beam energy may be used. Similarly, if a beam direction from a certain gantry angle traverses the tumor that is relatively far from the patient's skin, then higher beam energy may be used. For example, if a target is 2 cm under the patient's skin when viewed from a gantry position of 0°, and the same target is 3 cm under the patient's skin when viewed from a gantry position of 90°, then the system 10 may deliver beam with energy of 6 MV when the gantry 12 is at gantry angle of 0°, and may deliver beam with energy of 15 MV when the gantry 12 is at gantry angle of 90°.

In some embodiments, the system 10 is configured to provide radiation beam for treating the patient without using any flattening filter. In other embodiments, the system 10 may be configured to flatten an energy profile across a cross-section of the beam before delivering the beam to treat the patient. The flattening may be achieved using one or more flattening filters. In one implementation, different filters for different respective beam energies may be provided. A mechanical positioner may be configured to place a selected one of the flattening filters (i.e., selected based on the beam energy level) at a beam path to thereby flatten the treatment beam.

Figure 2B:
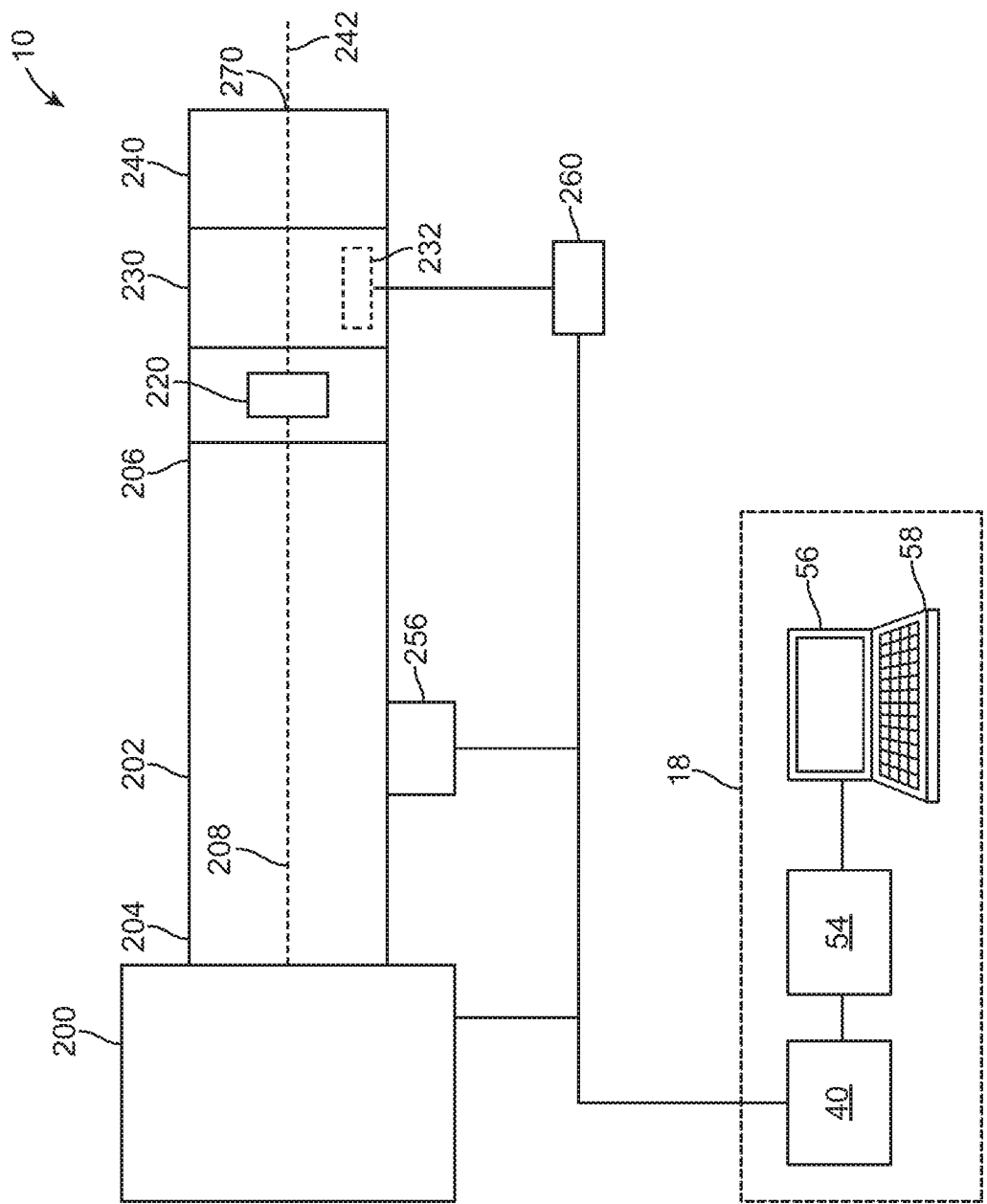
FIG. 2B illustrates another example of some of the components of the system of FIG. 1.

It should be noted that the configuration of the system 10 is not limited to the example described, and that the system 10 may have other configurations in other embodiments. For example, in other embodiments, the radiation treatment system 10 may not include the beam deflector 210. Instead, the accelerator 202 may be configured to provide the electron beam 208 directly to the target 220 without going through any beam deflector at the second end 206 of the accelerator 202 (FIG. 2B). Removing the beam deflector is advantageous because it may allow intra field switching of energy to be more easily implemented. In some embodiments, the switching of energy may be implemented while the gantry is continuously moving (e.g., as in RapidArc treatments).

Also, in other embodiments, the accelerator 202 may be a fixed-field alternating gradient (FFAG) accelerator, or a non-scaling fixed-field alternating gradient (NS-FFAG) accelerator.

Figure 3:
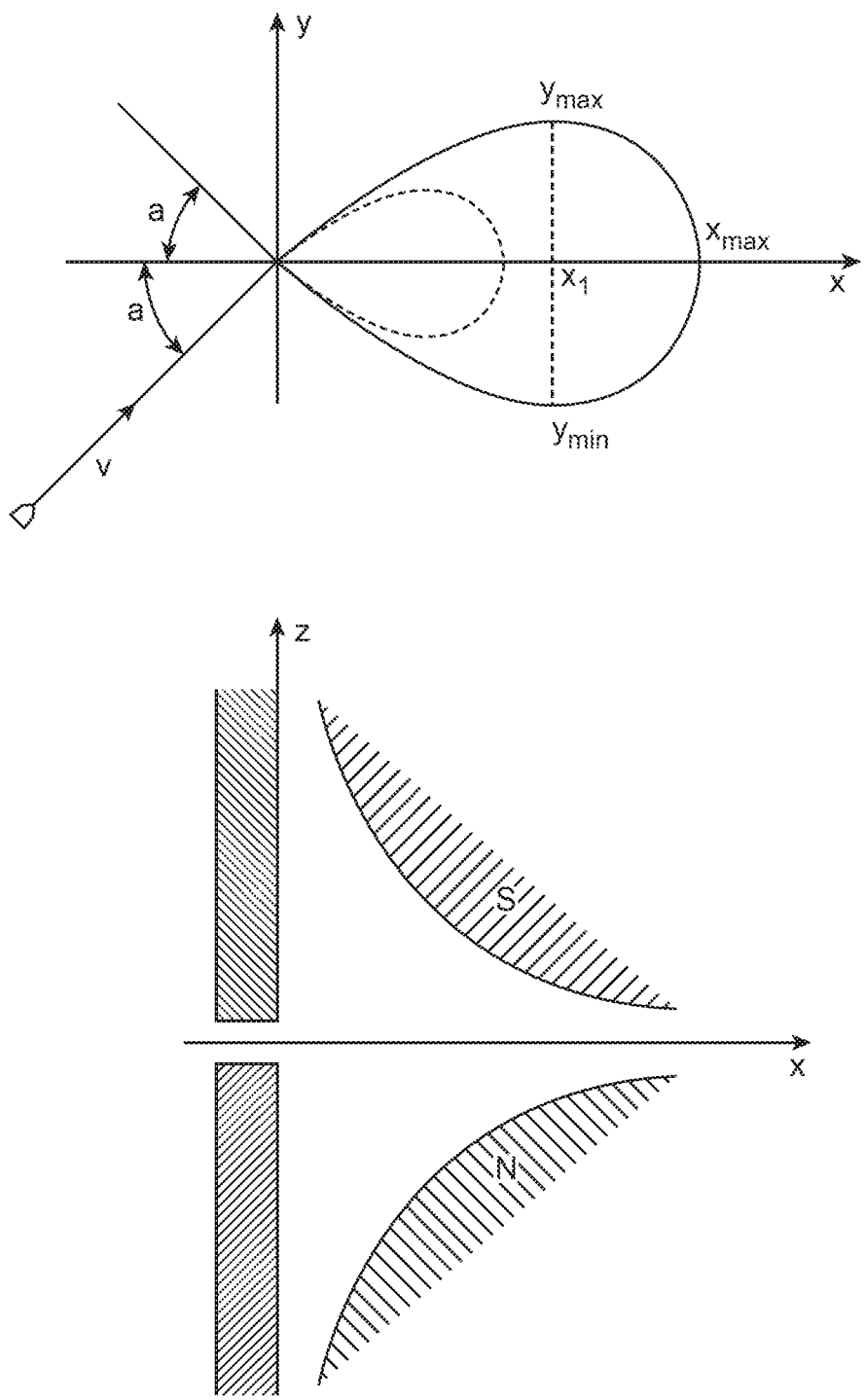
FIG. 3 illustrates an example of a pretzel magnet.

As discussed, in some embodiments, the beam deflector 210 may include both the electromagnet 212 and the permanent magnet 214. In some embodiments, one or each of the electromagnet 212 and the permanent magnet 214 may be implemented using an Enge mirror or pretzel magnet (FIG. 3). As shown in the figure, the principle of the Enge pretzel magnet is that a charged particle entering a field increasing with x will exit at the same angle as it entered, if the angle is a specific function of the field gradient.

Also, it should be noted that in addition to the beam deflector 210 and the dosimetry circuit 232, the system 10 may be configured to adjust other components based on a desired energy level. For example, in some embodiments, the system 10 may be configured to adjust beam steering servos based on an energy level of the beam being provided or to be provided.

Figure 4:
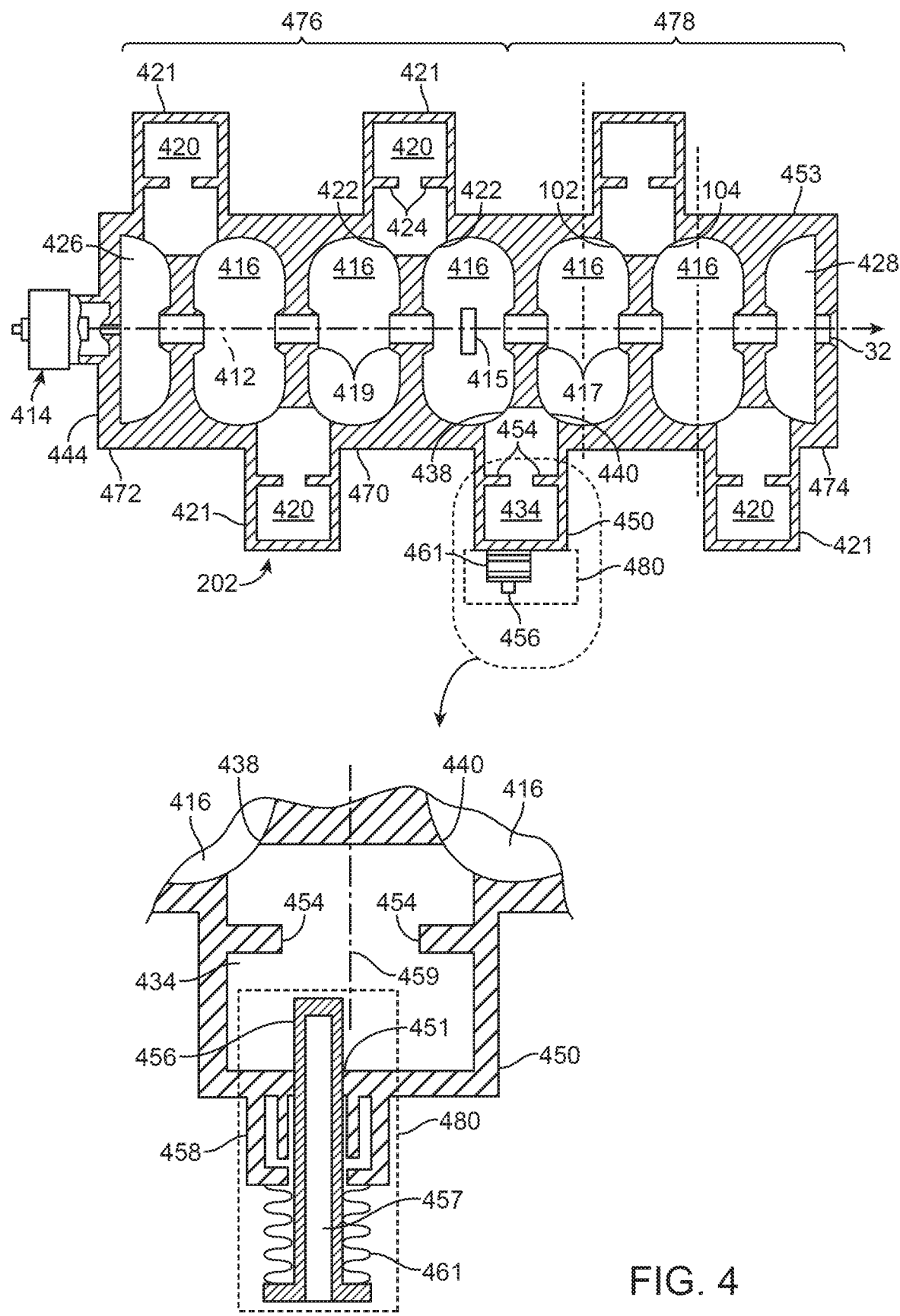
FIG. 4 illustrates an example of an accelerator having an energy switch.

FIG. 4 is a schematic axial sectional view of an example of the accelerator 202 of FIG. 1. The accelerator 202 comprises a main body 470 having a first end 472, a second end 474, and a chain of electromagnetically coupled resonant cavities (electromagnetic cavities) 416 between the first and second ends 472, 474. The accelerator 202 also includes a plurality of coupling bodies 421, each of which having a coupling cavity 420 that couples to two adjacent cavities 416. The accelerator 202 also has an energy switch 480 (which may be an example of the energy switch 256 of FIG. 1). The accelerator 202 is excited by microwave power delivered by a microwave source at a frequency near its resonant frequency, for example, between 1000 MHz and 20 GHz, and more preferably, between 2800 and 3000 MHz. The accelerator 202 may be excited by power having other levels in other embodiments by an energy source. The microwave source can be a Magnetron or a Klystron, both of which are known in the art. The power enters one cavity 416, preferably one of the cavities along the chain, through an opening 415.

In some embodiments, the accelerator 202 is configured to be operated with an automatic frequency control, such as that described in U.S. Pat. No. 3,820,035, for controlling an operation of a microwave source. The automatic frequency control helps the microwave source (or the RF driver) determine the accelerator 202 resonance by developing an error voltage that tracks a frequency error. The U.S. Pat. No. 3,820,035 is expressly incorporated by reference herein. Alternatively, or additionally, a control, such as that disclosed in U.S. Pat. No. 3,714,592, can be provided to provide feedback to the microwave source (e.g., a Magnetron) by deflecting some of the reflected signal generated by the accelerator 202, and sending it back into the microwave source. U.S. Pat. No. 3,714,592 is expressly incorporated by reference herein.

In some embodiments, the wall 444 of the main body 470 adjacent to a gun source 414 (which may be an example of the electron source 200 of FIG. 1) can include one or more pump out holes (not shown) for improving molecular flow conductance. In such cases, the accelerator 202 can further include a tuning ring (not shown) secured to an interior surface of the wall 444 for compensating the detuning from the pump out holes. The tuning ring can be manufactured with the wall 444 as a single unit. Alternatively, the tuning ring and the wall 444 can be manufactured separately, and then assembled together. Also, in some embodiments, the accelerator 202 can further include a copper plate, such as that described in U.S. Pat. No. 3,546,524, disposed at the interior face of the wall 444. The copper plate functions to terminate and shape the electric field.

During use, a linear beam 412 of electrons is injected into the accelerator 202 by a electron gun source 414 at the first end 472. The beam 412 may be either continuous or pulsed. The beam 412 passes through a first section 476 of the accelerator 202 in which electrons are captured and accelerated, and enters a second section 478 of the accelerator 202 where the captured electrons are further accelerated. Amplitude of the electric field in the second section 478 (i.e., downstream) can be adjusted by operation of the energy switch 480. Since the formation of electron bunches from an initial continuous beam takes place in the first section 476 of the accelerator 202, the bunching can be accomplished and/or optimized there and not degraded by the varying accelerating field in the output cavities 416 of the second section 478. The spread of energies in the output beam is thus made independent of the varying mean output electron energy. By controlling the RF power input (which changes the relative electric field between the first and second sections 476, 478), and the energy switch 480 (which changes the electric field in the second section 478), one can optimize spectrum of energies and maintain stable charging (or filling) of the accelerator 202.

In some embodiments, the accelerator 202 may optionally include a field step control to provide a change in the electric field (e.g., a stepped field) to decrease the range of field variation associated with operation of the energy switch 480. This use of field step has an effect of decreasing separations of resonant modes of the accelerator 202, so that an optimum range of beam energies can be generated. This in turn results in a relatively stable bandwidth, allowing the accelerator 202 to generate x-ray beam with a wider range of energy levels and minimum energy spread. In some embodiments, the field step control enables the accelerator 202 to provide x-ray beam or a particle beam (e.g., electron beam, proton beam, etc.) having an energy level that ranges from approximately 4 to 20 MeV. In other embodiments, the x-ray beam may have an energy level that is below 4 MeV (e.g., 2 MeV, or in the kV range). In further embodiments, the x-ray beam may have an energy level that is higher than 20 MeV. In some embodiments, the field step control is located further away from the beam source 414 than the energy switch 480, and is positioned adjacent to the energy switch 480. Alternatively, the field step control may be located at other positions, such as between the beam source 414 and the energy switch 480, or further downstream from the energy switch 480. The field step control may be implemented using different sizes and/or shapes of openings that are coupling between a side cavity and two adjacent main cavities, using a ring that is secured to a dividing wall separating adjacent cavities, using a nose (secured to a dividing wall that separates adjacent cavities) with a different size and/or shape compared to that of an adjacent nose, and/or using a beam aperture with a different size and/or shape compared to that of an adjacent beam aperture. Field step controls have been described in U.S. Pat. No. 7,339,320, the entire disclosure of which is expressly incorporated by reference herein.

In the illustrated embodiments, the electromagnetic cavities 416 are doughnut shaped with aligned central beam apertures 417 which permit passage of the beam 412. The cavities 416 may have projecting noses 419 of optimized configuration in order to improve efficiency of interaction of the microwave power and electron beam. The cavities 416 are electromagnetically coupled together through the coupling cavities 420, each of which is coupled to each of the adjacent pair of cavities 416 by an opening 422. The coupling cavities 420 are resonant at the same frequency as the accelerating cavities 416 and do not interact with the beam 412.

The frequency of excitation is such that the chain is excited in standing wave resonance with a π/2 radian phase shift between each coupling cavity 420 and the adjacent accelerating cavity 416. Thus, there is a π radian shift between adjacent accelerating cavities 416. The π/2 mode has several advantages. It has the greatest separation of resonant frequency from adjacent modes which might be accidentally excited. In other embodiments, the shift between adjacent cavities 416 may have other values. Also, when the chain is properly terminated, there are very small electromagnetic fields in coupling cavities 420 so the power losses in these non-interacting cavities are small. The first and last accelerating cavities 426 and 428 are shown as having one-half of an interior cavity 416. It is of course understood that, in alternative embodiments, the terminal cavities 426, 428 may each be a full cavity or any portion of a cavity. The spacing between accelerating cavities 416 is about one-half of a free-space wavelength, so that electrons accelerated in one cavity 416 will arrive at the next accelerating cavity in right phase relative to the microwave field for additional acceleration. Alternatively, the accelerating cavities 416 can have other spacing. In some embodiments, most of the accelerating cavities 416 and most of the coupling cavities 420 are similar such that the fields in most of the accelerating cavities 416 are substantially the same. Alternatively, the accelerating cavities 416 and/or the coupling cavities 420 can have other configurations such that the fields in some of the cavities 416 are different.

In the illustrated embodiments, the first section 476 (i.e., the "buncher" section) has 3½ cavities 416, and the second section 478 (i.e., the "accelerating" section) of the accelerator 202 has 2½ cavities 416. Alternatively, each of the sections 476, 478 of the accelerator 202 can have other number of cavities 416.

The energy switch 480 of the accelerator 202 is mounted to a cylindrical cup-shaped body 450 having a cavity 434 and an opening 451, and includes a probe 456 inserted through the opening 451, and a choke 458 coaxially surrounding at least part of the probe 456. The choke 458 is a double quarter-wave choke configured to facilitate transmission of high current around the opening 451 by functioning as an impedance transformation of short circuit to opened circuit. The body 450 is attached to the main body 470 of the accelerator 202 such that the cavity 434 is coupled to adjacent cavities 416 through respective openings 438, 440. The energy switch 480 also includes a pair of axially projecting conductive capacitively coupled noses 454 having opposed end faces that extend axially into the cavity 434. The body 450 and the noses 454 are similar to the body 421 and noses 424 discussed previously. In some embodiments, the cavity 434 (the switched side-cavity) is tuned to the same frequency as are the other coupling cavities 420. Such can be accomplished, for example, by varying a diameter or cross sectional dimension of the probe 456 when the probe 456 is at least partially inserted into the cavity 434. Alternatively, the tuning can be accomplished by varying separation between the noses 454 when the probe is not inserted into the cavity 434.

The probe 456 is positioned such that it is offset from a center line 459 of the body 450. In the illustrated embodiments, the probe 456 is located upstream of the center line 459 of the body 450. Alternatively, the probe 456 can be located downstream of the center line 459. The probe 456 is preferably circular cylinder although it could have other cross sectional shapes. In the illustrated embodiments, the probe 456 is made from stainless steel, but can also be made from other materials. The probe 456 has a lumen 457 extending along its length. During use, cooling fluid can be delivered into the lumen 457 (e.g., via another tube inserted coaxially into the lumen 457) for cooling of the probe 456. In alternative embodiments, the probe 456 has a solid cross section and does not have a lumen. The use of a single probe provides physical room for the mechanisms which engage the end of the probe 456 to advance and retract the probe 456 without mechanical interference. The mechanism (not shown) can comprise electrically actuated solenoid(s) or pneumatically operated cylinder(s). Movement of the probe 456 is through the vacuum wall via bellows 461, which provides a vacuum seal. During use, the pair of noses 454 function as coupling resonators, and the probe 456 functions as a third resonator. By varying a degree of insertion of the probe 456 into the cavity 434, distances between the probe 456 and the noses 454 change correspondingly, thereby altering the magnetic fields which couple to the openings 438, 440. This in turn alters the energy level of the beam downstream from the switch 480.

It should be noted that the type of switch that can be employed with the accelerator 202 is not necessarily limited to the example discussed previously, and that other types of switches known in the art can also be used. By means of non-limiting examples, accelerator switches such as those described in U.S. Pat. Nos. 4,382,208, 4,286,192, US 2007/0215813 can be used. U.S. Pat. No. 6,366,021 teaches switching electric fields in a coupling cavity by inserting two probes of selected diameter to provide different upstream and down stream electric field coupling to adjacent accelerating cavities. U.S. Pat. Nos. 6,366,021, 4,382,208, and 4,286,192, and US 2007/0215813 are expressly incorporated by reference herein. Also, in alternative embodiments, the energy switch 256 can be located at other position along the length of the accelerator 202, instead of that shown in the illustrated embodiments. Furthermore, although only one energy switch is shown in the previously described embodiments, alternatively, the accelerator 202 can have a plurality of energy switches.

Figure 5:
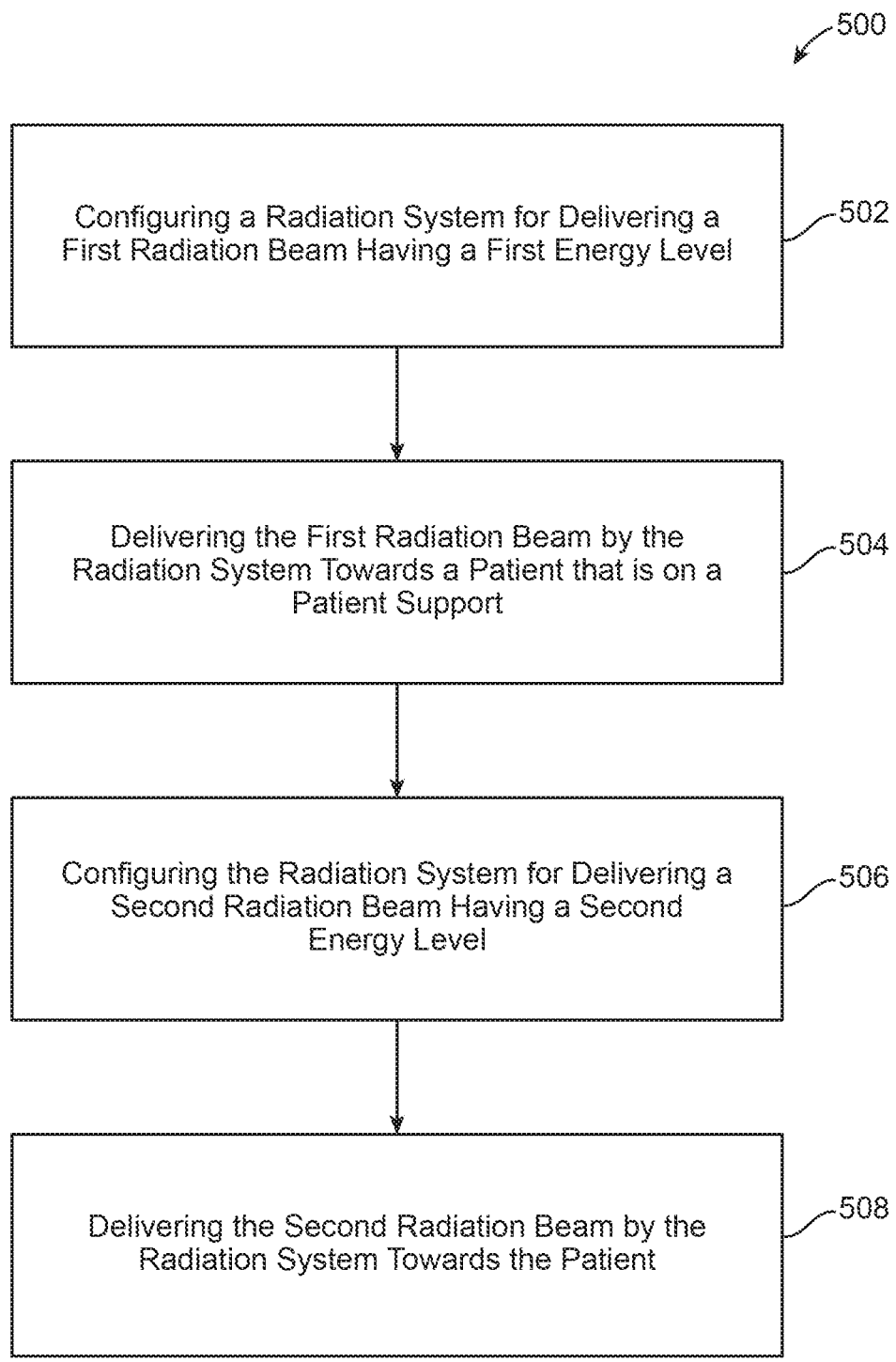
FIG. 5 illustrates a treatment method.

FIG. 5 illustrates a treatment method 500 that may be performed by the radiation treatment system 10. The treatment method 500 includes configuring a radiation system for delivering a first radiation beam having a first energy level (item 502); delivering the first radiation beam by the radiation system towards a patient that is on a patient support (item 504); configuring the radiation system for delivering a second radiation beam having a second energy level (item 506); and delivering the second radiation beam by the radiation system towards the patient (item 508). In some embodiments, the act of configuring the radiation beam for delivering the second radiation beam in item 506 comprises changing an energy that is associated with the accelerator 202 by the energy switch 256, and adjusting a current of the electromagnet 212 by the current control 258 in correspondence with the energy associated with the accelerator 202. The adjustment of the current may occur before, after, or simultaneously with, the adjustment of the energy that is associated with the accelerator 202 by the energy switch 256. In some cases, the switching of energy may be performed between treatment delivery fields using a fast and automated method. Alternatively or additionally, the switching of energy may be performed during an treatment delivery field.

In some embodiments, the first radiation beam in item 504 is delivered towards the patient from a first gantry angle, and the second radiation beam in item 508 is delivered towards the patient from a second gantry angle. In other embodiments, the first radiation beam in item 504 is delivered towards the patient from a first gantry angle, and the second radiation beam in item 508 is delivered towards the patient from the first gantry angle.

Also, in some embodiments, the treatment system 10 comprises the ion chamber 230 with the dosimetry circuit 232. In such cases, the method 500 further comprises adjusting a parameter in the dosimetry circuit 232 in correspondence with the energy associated with the accelerator 202. The adjusting of the parameter in the dosimetry circuit 232 may occur before, after, or simultaneously with, the adjustment of the current for the electromagnet 210.

In some embodiments, the acts of configuring the radiation system 10 (items 502, 506), and the acts of delivering (items 504, 508) are performed so that the first radiation beam transitions to the second radiation beam in a continuous manner. In other embodiments, the acts of configuring the radiation system 10 (items 502, 506), and the acts of delivering (items 504, 508) are performed so that the first radiation beam and the second radiation beam are delivered in discrete manner.

Figure 6:
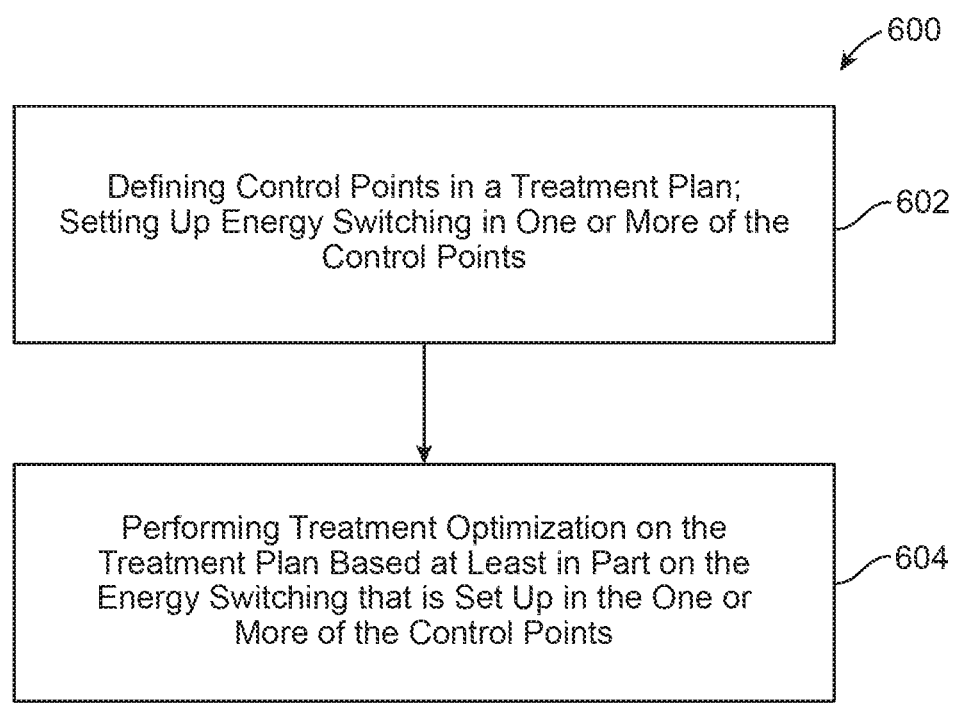
FIG. 6 illustrates a treatment planning method.

FIG. 6 illustrates a treatment planning method 600. The method 600 includes defining control points in a treatment plan; setting up energy switching in one or more of the control points (item 602); and performing treatment optimization on the treatment plan based at least in part on the energy switching that is set up in the one or more of the control points (item 604). In some embodiments, a user interface may be provided that allows a user to define the control points in the treatment plan, and to set up energy switching in one or more of the control points. Also, in some embodiments, the features (e.g., control points, and energy switching parameters) of the treatment plan, and the treatment plan itself, may be stored in a non-transitory medium for later use.

In some embodiments, the act of setting up energy switching in item 604 comprises prescribing the energy switching between two gantry positions. In other embodiments, the act of setting up energy switching comprises prescribing the energy switching at a same gantry position.

Also, in some embodiments, the energy switching is set up in item 604 so that the treatment plan will include a delivery of a first energy beam for treating a patient, and a delivery of a second energy beam for treating the patient.

Figure 7:
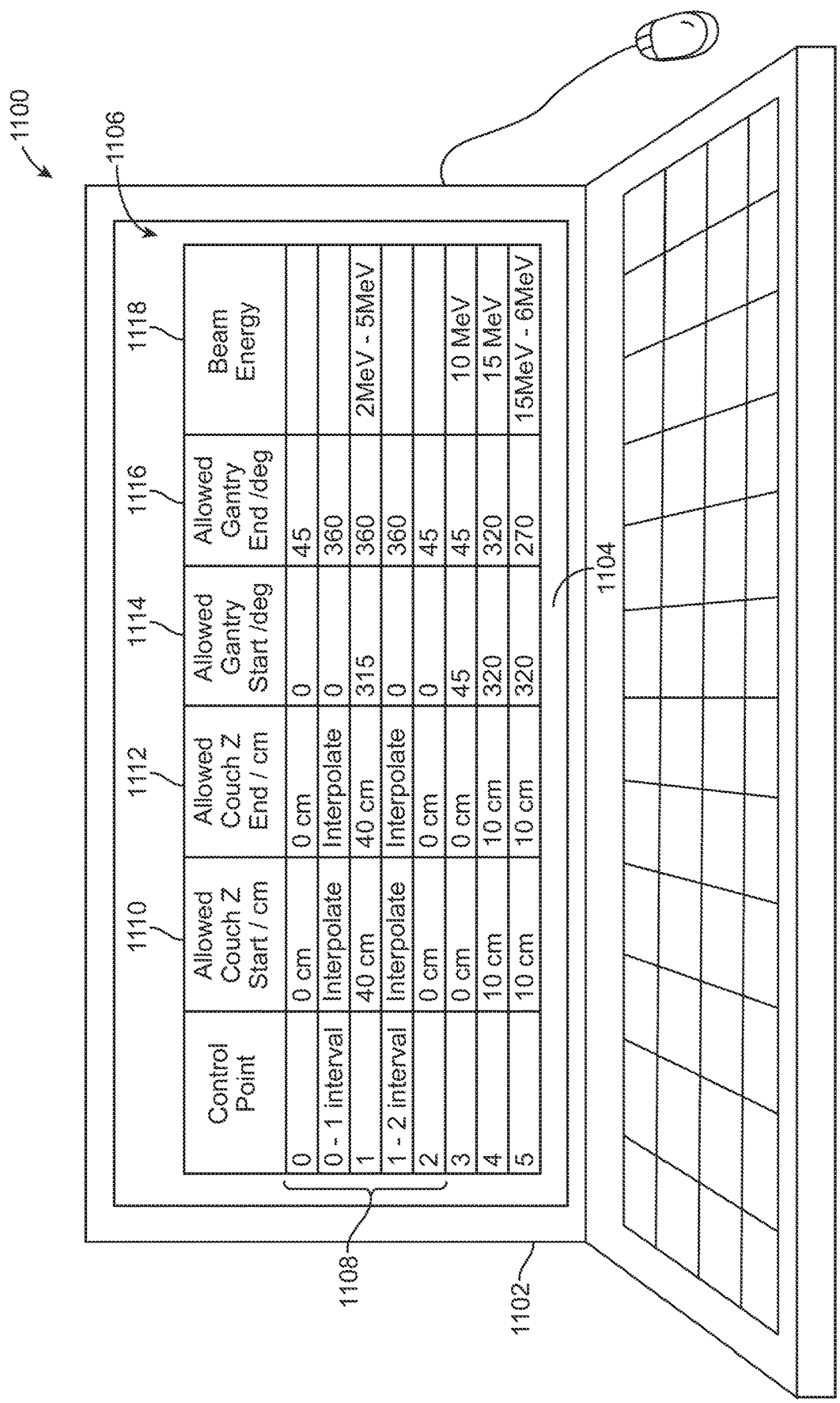
FIG. 7 illustrates an example of user interface for determining a treatment plan.

FIG. 7 illustrates an example of a user interface 1100 that may allow a user to determine a treatment plan in accordance with some embodiments. As used in this specification, the term "user" may refer to a single person, or a plurality of persons. In some cases, the user interface 1100 may be used in the method 600 to determine a treatment plan. The user interface 1100 includes a screen 1102 displaying an input interface 1104. The input interface 1104 may be generated by a processor that executes a set of instruction programmed to provide the image of the input interface 1104. In the illustrated embodiments, the input interface 1104 includes a table 1106 having fields that allow the user to input parameters and/or values. In the illustrated example, the user has defined in table 1106 control points 1108, parameter 1110 for the allowable starting point of support 14, parameter 1112 for allowable ending point of support 14, parameter 1114 for allowable gantry starting angle, and parameter 1116 for allowable gantry ending angle. As shown in the example, a control point may represent treatment parameter(s) at a given time, dose, gantry angle, etc., or an interval between two points of varying treatment parameters (e.g., "0-1 interval," "1-2 interval"). The table 1106 includes various input fields for allowing the user to input values for the parameters at different control points. As shown in the example, a value may be a numerical value, or an instruction (e.g., "interpolate"—which specifies that values for the corresponding control point are to be calculated in accordance with a prescribed scheme). In some embodiments, the user needs not enter all or any value for the input fields. In such cases, the processor/software for determining the treatment plan is configured to determine the values for the various fields in the table 1106.

In the illustrated example, a trajectory is defined by the control points 1108, wherein each control point 108 defines a region in parameter space. The optimized trajectory has to pass through the defined region before proceeding to the next control point 108. The allowed region (range of parameters) between the control points is also defined. Thus, the control points define the region where the machine control points must be placed. In some cases, the processor/software for determining the treatment plan is configured to generate machine control points based on these rules and the defined parameters. For example, the processor/software may perform optimization based on geometric properties of target region(s) and healthy region(s). The processor/software may then continue with the optimization using dose based method(s), e.g., direct aperture method, fluence based method, etc. In some cases, the processor/software may perform Pareto optimization, or any of other types of multi-criteria optimization. In some embodiments, the user interface 1100 allows the user to input initial values for some or all of the parameters. During the optimization process, the processor/software optimizes the values based on certain user-defined constraints (e.g., size, shape, and location of target, path of source, etc.). In other embodiments, the processor/software may be configured to determine the values for the parameters without any initial input values from the user.

In the illustrated example of FIG. 7, the trajectory would move the support 14 from 0 cm to 40 cm in the Z direction (from control point 0 to control point 1), and back to 0 cm (from control point 1 to control point 2). The gantry 12 would rotate from somewhere between 0° and 45° to between 315° and 360°, and back to between 0° and 45°. The Z-positions of the support 14 would be interpolated (e.g., linearly, or using some other interpolation scheme) between the control points. The trajectory then would move the gantry to 45° where treatment beam is to be delivered at 10 MeV (control point 3). The trajectory then would move the patient support in the Z direction to position 10 cm, and would move the gantry to 320° where treatment beam is to be delivered at 15 MeV (control point 4). The trajectory then would move the gantry from 320° to 270°, where through this gantry range, the treatment beam is to be delivered at energy level that ranges from 15 MeV to 6 MeV.

In some embodiments, the optimizer of the processor/software that is used to perform method 600 is configured to determine the route between the control points for gantry angles in the 0° to 360° interval.

In some cases, the user interface 1100 also allows the user to perform simple operations on defined trajectory. For example, in some embodiments, the trajectory of FIG. 7 may be stretched in the Z-direction by applying a multiplication of 2 in the Z-direction of the support 14. In other embodiments, at least part of the trajectory may be shifted.

In some embodiments, the user interface 1100 allows the user to save the designed trajectory in a medium. The trajectory may be saved as a part of a treatment plan, which will be used later in a treatment procedure. Alternatively, or additionally, the trajectory may be saved as a trajectory class. In some cases, the trajectory classes may be organized based on specific machines (e.g., different machines may have different classes of trajectories), patient anatomy, location of target regions, sizes of target regions, shapes of target regions, and/or other disease specific factors. In such cases, a user may retrieve a trajectory from one of the available trajectory classes, based on the specific machine, target region's shape, size, and location, and type of disease. The user may then revise the retrieved trajectory to fine-tune it so that is can be better used for a specific treatment for a specific patient. For example, the user may perform a multiplication and/or an adding procedure for any part (e.g., a parameter type) of the trajectory, to thereby fit the dimensions and/or positions of a target in a specific patient.

It should be noted that the type of parameters that may be defined using the user interface 1100 is not limited to the example discussed, and that the user interface 1100 may allow the user to define other parameters, such as gantry angle, positions (e.g., x, y, z) of support 14, orientations ($O_x$, $O_y$, $O_z$) of support 14, dose (e.g., user may specify whether dose is to be delivered for a control point), dose rate, leaves' positions, and speed limits (e.g., of gantry rotation, leaves movements, support 14 movements, etc.). Also, the user interface 1100 may allow the user to prescribe whether to provide a constant energy at a certain gantry angle, or to provide a variable energy at a certain gantry angle. The user interface 1100 may further allow the user to prescribe whether to provide a constant energy while rotating the gantry, or whether to provide a variable energy while rotating the gantry.

As illustrated in the above embodiments, the user interface 1100 provides a flexible method for a planner to communicate to the optimizer which class of trajectories is considered for a specific case. The trajectory is defined as a set of control points, in which some parameters are to be optimized, and other parameters are to be interpolated. Energy switching may be implemented as one or more parameters through the user interface 1100. In some embodiments, parameters that are not optimized are interpolated using an interpolation scheme. The user interface 1100 also allows ranges to be defined, and provides tools for a user to manipulate the trajectory class. In some cases, the parameters to be optimized may be different for different intervals of the treatment. Thus, the user interface 1100 provides a tool for allowing a user to define a trajectory that is flexible enough for different applications, and is easy to converge to a good solution (because not all of the parameters need to be optimized—some of the parameters may be interpolated).

Specialized Processing System

Figure 8:
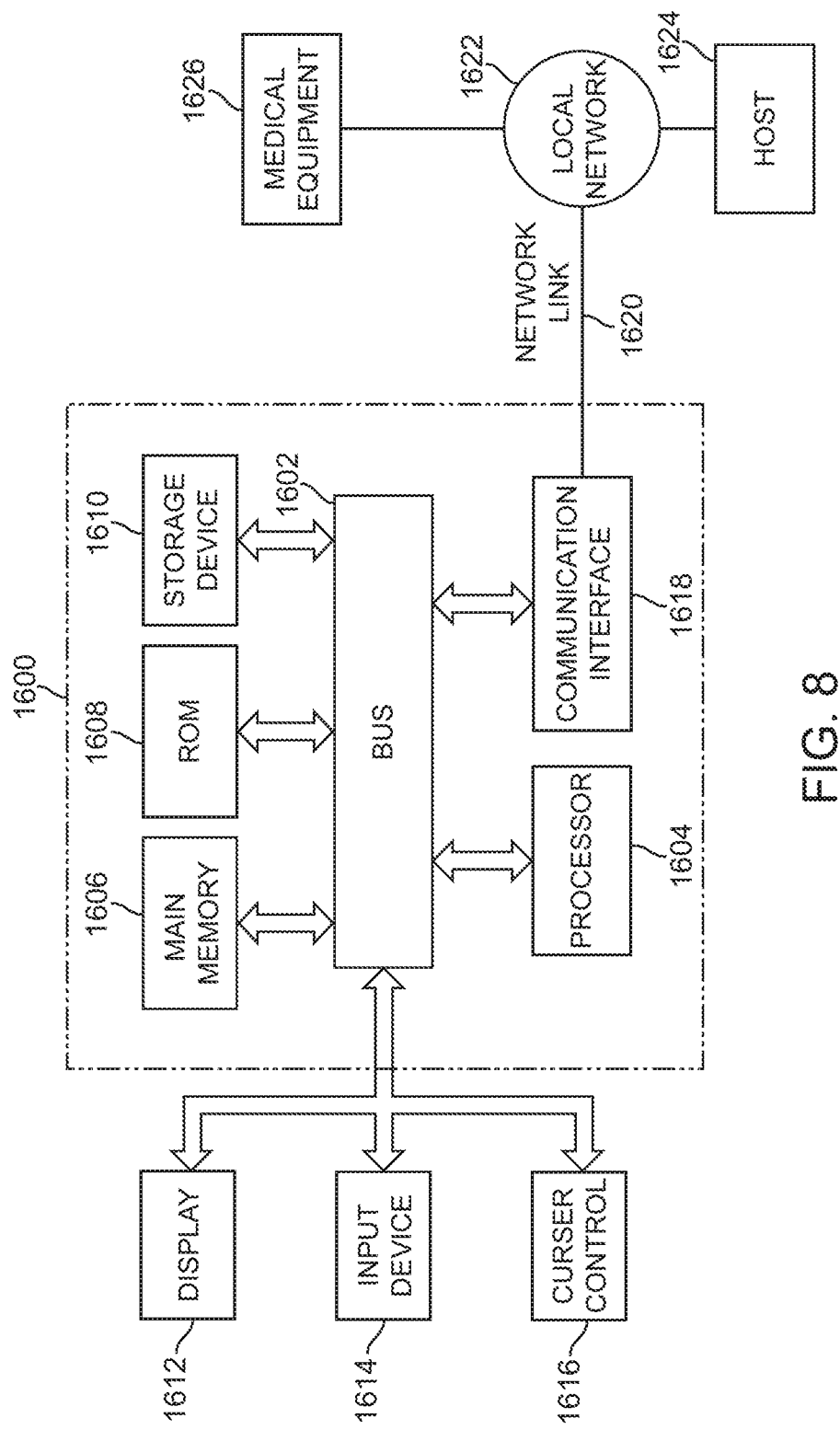
FIG. 8 illustrates an example of a specialized processing system with which one or more embodiments described herein may be implemented.

FIG. 8 is a block diagram illustrating an embodiment of a specialized processing system 1600 that can be used to implement various embodiments described herein. For example, the processing system 1600 may be configured to perform the method 500 of FIG. 5, and/or the method 600 of FIG. 6. The processing system 1600 may also be an example of the processing unit 54 (or a component thereof), an example of the current control 258 (or a component thereof), and/or an example of the control 260 (or a component thereof). The processing system 1600 may also be any processor described herein.

Referring to FIG. 8, the processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

It should be noted that as used in this specification, the term "beam", or any of other similar terms, may refer to one or more beam(s). For example, the system 10 may deliver a treatment beam towards the patient, and may vary the energy of the treatment beam from a first energy level to a second energy level. In such cases, the treatment beam may considered as a single treatment beam with variable energies, or alternatively, as a first beam having the first energy level and a second beam having the second energy level. The above definition applies even in the scenario in which different energy beams are delivered discretely. For example, the system 10 may deliver a first treatment beam having a first energy level, and then stop the treatment beam delivery. The system 10 may then deliver a second treatment beam having a second energy level. In this scenario, the system 10 may be considered as delivering multiple energy beams at different respective energies, or alternatively, as delivering a treatment beam having different instances of deliveries and different energy levels. Also, in some embodiments, a treatment beam may be a photon beam (e.g., x-ray beam), a particle beam (e.g., electron beam, proton beam, etc.), or a combination of a photon beam and a particle beam.

Also, the various features described with reference to the beam deflector 210 may be incorporated into other radiation systems in other embodiments, and they are not limited for application to radiation systems with energy switching. For example, the rare earth magnet, the hybrid magnet, etc. may be utilized in any radiation system, with or without energy switching.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A method performed by a medical device, the method comprising:
adjusting an energy level of a particle beam within an accelerator to a first value with an energy switch communicatively coupled to the accelerator;
providing the particle from the accelerator to a beam deflector, the beam deflector including a permanent magnet and an electromagnet;
providing a permanent magnetic field by the permanent magnet;
operating the electromagnet to provide a first electromagnetic field with a first electromagnetic field value based on the first value of the particle beam;
adjusting the energy level of the particle beam within the accelerator to a second value with the energy switch; and
operating the electromagnet to provide a second electromagnetic field with a second electromagnetic field value based on the second value of the energy level of the particle beam;
wherein the first electromagnetic field with the first electromagnetic field value and the permanent magnetic field forms a first total magnetic field with a first total magnetic field value, and wherein the second electromagnetic field with the second electromagnetic field value and the permanent magnetic field forms a second total magnetic field with a second total magnetic field value.

2. The method of claim 1, wherein the permanent magnet comprises a rare earth magnet.

3. The method of claim 1, wherein the electromagnet comprises a coil surrounding the permanent magnet.

4. The method of claim 1, wherein the energy level of the particle beam is changed within a duration that is less than one second.

5. The method of claim 1, wherein the accelerator comprises a fixed-field alternating gradient (FFAG) accelerator, or a non-scaling fixed-field alternating gradient (NS-FFAG) accelerator.

6. The method of claim 1, further comprising adjusting a parameter in a dosimetry circuit based on an electric field in the accelerator or the energy level of the particle beam.

7. The method of claim 6, wherein the dosimetry circuit is a part of an ion chamber.

8. The method of claim 1, wherein the electromagnet comprises laminated steel.

9. The method of claim 1, wherein the operating the electromagnet comprises increasing a current of the electromagnet based on an increase in an electric field in the accelerator or the energy level of the particle beam.

10. The method of claim 1, wherein the operating the electromagnet comprises decreasing a current of the electromagnet based on a decrease in an electric field in the accelerator or the energy level of the particle beam.

11. The method of claim 1, wherein the electromagnet comprises a pretzel magnet.

12. The method of claim 1, wherein a beam output is coupled to the beam deflector, and wherein the method further comprises moving the beam output to deliver treatment energy from a plurality of gantry angles that includes at least a first gantry angle and a second gantry angle.

13. The method of claim 12, further comprising adjusting the treatment energy so that the treatment energy has a first treatment energy level when the beam output is at the first gantry angle, and a second treatment energy level when the beam output is at the second gantry angle.

14. The method of claim 13, wherein the treatment energy is adjusted by an energy adjuster in a continuous manner.

15. The method of claim 13, wherein the treatment energy is adjusted by an energy adjuster in a discrete manner.

16. The method of claim 12, further comprising adjusting the treatment energy so that the treatment energy has a first treatment energy level when the beam output is at the first gantry angle, and a second treatment energy level when the beam output is at the first gantry angle.

17. The method of claim 12, wherein the treatment energy is outputted without using any flattening filter.

18. The method of claim 1, wherein the electromagnet is operated such that a trajectory of the particle beam remains constant regardless of an energy level of an electric field in the accelerator or the energy level of the particle beam.

19. A treatment method, comprising:
configuring a medical system for delivering a first treatment beam having a first energy level from an accelerator, including
delivering the first treatment beam to a beam deflector, the beam deflector including a permanent magnet and an electromagnet;
delivering the first treatment beam by the medical system from the beam deflector towards a patient that is on a patient support;
configuring the medical system for delivering a second treatment beam having a second energy level from the accelerator to the beam deflector, including
changing the first energy level to the second energy level with an energy switch communicatively coupled to the accelerator, and
adjusting a current of the electromagnet with a current control communicatively coupled to the beam deflector based on the second energy level; and
delivering the second treatment beam by the medical system towards the patient;
wherein the first treatment beam is delivered towards the patient from a first gantry angle, and the second treatment beam is delivered towards the patient from a second gantry angle.

20. The method of claim 19, wherein the medical system comprises an ion chamber, wherein the ion chamber comprises a dosimetry circuit, and wherein the method further comprises adjusting a parameter in the dosimetry circuit based on an energy level associated with the accelerator.

21. The method of claim 19, wherein the delivering the first treatment beam and the delivering the second treatment beam are configured to be performed so that the first treatment beam transitions to the second treatment beam in a continuous manner.

22. The method of claim 19, wherein the delivering of the first treatment beam and the delivering of the second treatment beam are configured to be performed so that the first treatment beam and the second treatment beam are delivered in a discrete manner.

23. The method of claim 19, wherein the first or second energy level from the accelerator comprises an electric field in the accelerator or an energy level of a particle beam in the accelerator.

* * * * *